United States Patent [19]

Wild et al.

[11] 4,239,886
[45] Dec. 16, 1980

[54] SALTS OF N-ACYLAMINOHYDROXYNAPHTHALENE-SULPHONIC ACIDS

[75] Inventors: Peter Wild, Alten Buseck; Horst Nickel, Leverkusen, both of Fed. Rep. of Germany

[73] Assignee: Bayer Aktiengesellschaft, Leverkusen, Fed. Rep. of Germany

[21] Appl. No.: 12,946

[22] Filed: Feb. 16, 1979

[30] Foreign Application Priority Data

Feb. 18, 1978 [DE] Fed. Rep. of Germany ....... 2806951

[51] Int. Cl.³ .................. C07D 265/30; C07C 93/04; C07D 295/08
[52] U.S. Cl. .................. 544/170; 260/501.18; 260/326.5 S; 544/177; 546/206
[58] Field of Search ........... 260/509, 501.12, 326.5 S, 260/501.15, 501.18; 546/206; 544/170, 177

[56] References Cited

U.S. PATENT DOCUMENTS

| | | | |
|---|---|---|---|
| 2,842,536 | 7/1958 | Bauer et al. | 260/509 |
| 2,871,120 | 1/1959 | Coles et al. | 260/509 |
| 3,196,173 | 8/1965 | Willmund et al. | 260/509 |
| 3,277,075 | 10/1966 | Mayhew et al. | 260/509 |
| 3,679,420 | 7/1972 | Yokoyama | 260/509 |
| 4,051,123 | 9/1977 | Piller et al. | 260/509 |

*Primary Examiner*—Natalie Trousof
*Assistant Examiner*—G. T. Breitenstein
*Attorney, Agent, or Firm*—Sprung, Felfe, Horn, Lynch & Kramer

[57] ABSTRACT

Salts of N-acylaminohydroxynaphthalenesulphonic acids which, in the form of the free acid, correspond to the formula

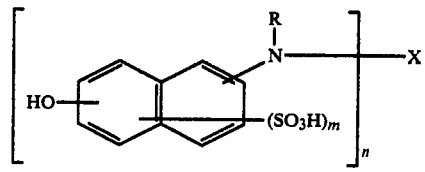

wherein
R denotes hydrogen or alkyl,
X denotes the radical of a monovalent or divalent acyl group,
m denotes 1 or 2 and
n denotes 1 or 2, and wherein at least one of the sulphonic acid groups contains, as a cation, a cation of the formula

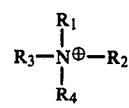

wherein
$R_1$ and $R_2$ independently of one another denote $C_1$-$C_4$-alkyl, $C_1$-$C_4$-alkoxy-$C_1$-$C_4$-alkyl or $R_3$, or
$R_1$ and $R_2$, together with the nitrogen atom, denote piperidinyl, morpholinyl or pyrrolinyl,
$R_3$ denotes the group

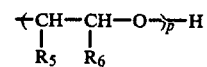

$R_4$ denotes hydrogen, $C_1$-$C_4$-alkyl, $C_1$-$C_4$-alkoxy-$C_1$-$C_4$-alkyl or the group

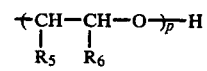

$R_5$ and $R_6$ denote hydrogen, methyl or ethyl and
p represents an integer between 1 and 10, a process for their preparation and their use as coupling components for the preparation of azo dyestuffs or concentrated solutions thereof.

7 Claims, No Drawings

SALTS OF N-ACYLAMINOHYDROXYNAPHTHALENESULPHONIC ACIDS

The invention relates to salts of N-acylaminohydroxy-naphthalenesulphonic acids which, in the form of the free acid, correspond to the formula

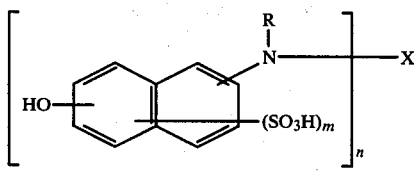

wherein
R denotes hydrogen or alkyl,
X denotes the radical of a monovalent or divalent acyl group,
m denotes 1 or 2 and
n denotes 1 or 2,
and wherein at least one of the sulphonic acid groups contains, instead of the proton, a cation of the formula

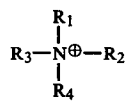

wherein
$R_1$ and $R_2$ independently of one another denote $C_1$-$C_4$-alkyl, $C_1$-$C_4$-alkoxy-$C_1$-$C_4$-alkyl or $R_3$, or
$R_1$ and $R_2$, together with the nitrogen atom, denote piperidinyl, morpholinyl or pyrrolinyl,
$R_3$ denotes the group

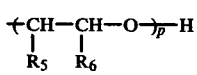

$R_4$ denotes hydrogen, $C_1$-$C_4$-alkyl, $C_1$-$C_4$-alkoxy-$C_1$-$C_4$-alkyl or the group

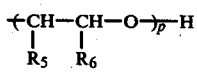

$R_5$ and $R_6$ denote hydrogen, methyl or ethyl and
p represents an integer between 1 and 10. If n denotes 2, the dyestuff can be built up from identical or non-identical aminohydroxynaphthalenesulphonic acids.

The new compounds of the formula (I) are obtained by a process in which the free acids are reacted with appropriate acylating agents in the presence of compounds of the formula

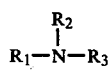

or their hydroxides quaternised by $C_1$-$C_4$-alkyl, $C_1$-$C_4$-alkoxy-$C_1$-$C_4$-alkyl or groups of the formula

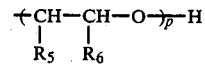

wherein
$R_1$, $R_2$, $R_3$, $R_5$, $R_6$ and p have the abovementioned meanings.

Suitable alkyl groups R are, in particular, $C_1$-$C_4$-alkyl, preferably methyl or ethyl.

Suitable monovalent acyl groups are $C_1$-$C_4$-alkylcarbonyl, and benzoyl which is optionally substituted by methyl, methoxy, chlorine or nitro. Suitable divalent acyl groups are —CO—CO—, —CO—, —CO—CH=CH—CO and terephthaloyl.

Possible acylating agents are the halides and anhydrides of aliphatic and aromatic carboxylic acids, the acyl radical of which corresponds to the above definition, as well as carbonic acid derivatives, such as phosgene or chloroformic acid methyl, ethyl or phenyl ester and oxalic acid dichloride, fumaric acid dichloride and terephthalic acid dichloride.

Examples of suitable aminohydroxynaphthalenesulphonic acids are 7-amino-4-hydroxy-2-naphthalenesulphonic acid, 8-amino-4-hydroxy-2-naphthalenesulphonic acid, 7-amino-3-hydroxy-1-naphthalenesulphonic acid, 7-methylamino-4-hydroxy-2-naphthalenesulphonic acid, 6-amino-4-hydroxy-2-naphthalenesulphonic acid, 6-amino-4-hydroxy-1-naphthalenesulphonic acid, 2-amino-5-hydroxy-1,7-naphthalenedisulphonic acid, 3-amino-8-hydroxy-1,5-naphthalenedisulphonic acid and 3-amino-5-hydroxy-2,7-naphthalenedisulphonic acid.

The acylation is appropriately carried out by dissolving or suspending the aminohydroxysulphonic acids, as the free acids, in water, rendering the solution or suspension neutral with the tertiary amine or its quaternised hydroxide, a polar organic solvent, such as dimethylformamide, sulpholane or glycol ethers being added if necessary, and adding the acylating agent. The acid liberated during the reaction is neutralised by adding the same or a different tertiary amine or its quaternary hydroxide and the pH value is kept between about 5 and 8. The reaction is appropriately carried out at temperatures between 20° and 80° C. It is also appropriate to choose the amount of water or solvent so that at least the end product is present in a concentrated, homogeneous solution.

Examples of suitable amines and quaternised ammonium hydroxides are triethanolamine, methyldiethanolamine, tris-propanol- or -isopropanol-amine, tris-[2-(2-hydroxyethoxy)ethyl]amine, diethyl- or dimethylethanolamine, N-hydroxyethylpiperidine, N-hydroxyethylmorpholine and the quaternary ammonium hydroxides mentioned in U.S. Pat. No. 3,995,997.

The compounds according to the invention are suitable, both in their isolated form and, in particular, in the form of concentrated aqueous or aqueous-organic solutions, as coupling components for the preparation of azo dyestuffs, in particular for the preparation of concentrated aqueous or aqueous-organic solutions of azo dyestuffs.

The concentrated solutions of the compounds according to the invention are stable on storage over a long period. The compounds according to the invention can be isolated from these solutions, by concentrating or cooling, in the solid or oily form, which is very readily soluble in water.

EXAMPLE 1

120 g of 7-amino-4-hydroxy-2-naphthalenesulphonic acid (I-acid) are dissolved in 200 ml and 50 ml of methyldiethanolamine at pH 7 to 8. Acylation is carried out with 60 ml of acetic anhydride at 30° to 40° C. in the course of 2 hours, and the pH value is kept at 5 to 6 with about 50 ml of methyldiethanolamine. Stirring is continued until no further I-acid can be detected. The concentrated acetyl-I-acid solution thus obtained can be further processed direct to dyestuffs. By cooling the mixture to temperatures below 0° C., the methyldiethanolammonium salt of acetyl-I-acid separates out and can be isolated as a light brown powder. If the water is distilled off from the solution, an oil is formed which becomes crystalline after some time.

EXAMPLE 2

120 g of I-acid are dissolved with 300 ml of water and about 50 to 60 ml of methyldiethanolamine at pH 7 to 8. Phosgene is passed in at 50° to 60° C. and the pH value is kept at 6 to 6.5 with methyldiethanolamine. When the I-acid content has fallen to less than 10%, the phosgenation is brought to completion at pH 7 in the course of about one hour. The I-acid-urea solution thus obtained is stable over a relatively long period. If it is cooled to temperatures below −5° C., the ammonium salt of the I-acid-urea separates out as crystals.

EXAMPLE 3

The procedure followed is as described in Example 1, but about 60 ml of benzoyl chloride are used as the acylating agent and the pH value is kept at 5 to 6 with 80 ml of methyldiethanolamine. After the reaction has ended, the ammonium salt of benzoyl-I-acid can be separated out of the solution as crystals at about 0° C. and with a little dilute hydrochloric acid.

EXAMPLE 4

159.5 g of 3-amino-8-hydroxy-1,5-naphthalenedisulphonic acid are dissolved in 300 ml of water and 138 ml of methyldiethanolamine at 50° C. and pH 6.5. Phosgene is passed into this solution at 50° C., and the pH value is kept at 6.5 with methyldiethanolamine, until no further starting material can be detected. The water is largely distilled off from the solution. After some time, the methyldiethanolammonium salt of 8,8'-dihydroxy-1,1',5,5'-tetrasulpho-3,3'-dinaphthylurea crystallises out of the viscous mass which remains.

EXAMPLE 5

120 g of 7-amino-4-hydroxy-2-naphthalenesulphonic acid are dissolved in 200 ml of water and about 150 ml of tris-[2-(2-hydroxyethoxy)-ethyl]-amine at pH 7 to 8. Phosgene is passed in at 50° to 60° C., and the pH value is kept at 6 to 7 by adding the same amine, until the starting material has been converted completely into the corresponding urea. The resulting solution of the urea is stable on storage over a relatively long period and also can be used direct as a coupling medium.

EXAMPLE 6

The procedure followed is as indicated in Example 2, but using N-hydroxyethylmorpholine as the amine. About 600 ml of a solution of the N-hydroxyethylmorpholinium salt of I-acid-urea are obtained.

EXAMPLE 7

120 g of 6-amino-4-hydroxy-1-naphthalenesulphonic acid are suspended in 200 ml of water and 120 ml of methyldiethanolamine at pH 8.5. Phosgene is passed in at 50° C., and the pH value is kept at 6.5, after it has fallen to this value, with methyldiethanolamine, until no further starting material is present. A clear solution of 4,4'-dihydroxy-1,1'-disulpho-6,6'-dinaphthylurea, as the methyldiethanol-ammonium salt, is thereby formed.

EXAMPLE 8

If 130 g of methyltriethanolammonium hydroxide are used in Example 7 instead of the methyldiethanolamine, a clear solution is likewise formed, 4,4'-dihydroxy-1,1'-disulpho-6,6'-dinaphthyl-urea being present as the methyltriethanolammonium salt.

We claim:

1. Salts of N-acylaminohydroxynaphthalenesulphonic acids which, in the form of the free acid, correspond to the formula

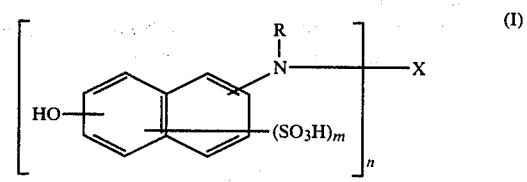

wherein
R denotes hydrogen or alkyl,
X denotes the radical of a monovalent or divalent acyl group,
m denotes 1 or 2 and
n denotes 1 or 2,
and wherein at least one of the sulphonic acid groups contains, as a cation, a cation of the formula

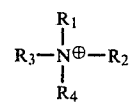

wherein
$R_1$ and $R_2$ independently of one another denote $C_1$-$C_4$-alkyl, $C_1$-$C_4$-alkoxy-$C_1$-$C_4$-alkyl or $R_3$, or
$R_1$ and $R_2$, together with the nitrogen atom, denote piperidinyl, morpholinyl or pyrrolinyl,
$R_3$ denotes the group

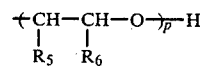

$R_4$ denotes hydrogen, $C_1$-$C_4$-alkyl, $C_1$-$C_4$-alkoxy-$C_1$-$C_4$-alkyl or the group

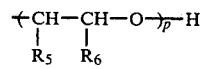

$R_5$ and $R_6$ denote hydrogen, methyl or ethyl and
p represents an integer between 1 and 10.

2. Concentrated aqueous or aqueous-organic solutions of the compounds according to claim 1.

3. A salt according to claim 1 which is the ammonium salt of 7-amino-4-hydroxy-2-naphthalenesulphonic acid urea.

4. A salt according to claim 1 wherein $R_1$ or $R_2$ represents alkyl, alkoxyalkyl or the moiety —$(CHR_5CHR_6O)_pH$.

5. A salt according to claim 1 wherein $R_1$ or $R_2$ represents piperidinyl.

6. A salt according to claim 1 wherein $R_1$ or $R_2$ represents morpholinyl.

7. A salt according to claim 1 wherein $R_1$ or $R_2$ represents pyrrolinyl.

* * * * *